United States Patent [19]

Hesse et al.

[11] 4,263,215
[45] Apr. 21, 1981

[54] PROCESS FOR THE PREPARATION OF 1-HYDROXYLATED VITAMIN D COMPOUNDS

[75] Inventors: Robert H. Hesse, Cambridge, Mass.; Graham Johnson, Milton Keynes, Great Britain

[73] Assignee: Research Institute for Medicine and Chemistry, Inc., Cambridge, Mass.

[21] Appl. No.: 91,743

[22] Filed: Nov. 6, 1979

[30] Foreign Application Priority Data

Nov. 7, 1978 [GB] United Kingdom ............... 43458/78

[51] Int. Cl.$^3$ .............................................. C07J 9/00
[52] U.S. Cl. .................................................. 260/397.2
[58] Field of Search ........................................ 260/397.2

[56] References Cited

U.S. PATENT DOCUMENTS

WO79/00 513  8/1979  De Luca et al. ..............260/397.2

OTHER PUBLICATIONS

"Steroids", published Aug. 1977, vol. 30, No. 2, pp. 193–201, by Pelc et al.

*Primary Examiner*—Elbert L. Roberts
*Attorney, Agent, or Firm*—Bacon & Thomas

[57] ABSTRACT

1-Hydroxy-5,6-trans vitamin D compounds are prepared by oxidizing a 5,6-trans vitamin D compound using a selenic ester which may be formed in situ using selenous acid or selenium dioxide in the presence of an alcohol.

15 Claims, No Drawings

PROCESS FOR THE PREPARATION OF 1-HYDROXYLATED VITAMIN D COMPOUNDS

The present invention relates to a process for the preparation of 1-hydroxylated Vitamin D compounds.

1α-Hydroxy vitamin D compounds, especially 1α-hydroxy vitamin D$_3$, are known to be useful in medicine for a variety of purposes and, for example, possess important prophylactic and therapeutic applications in the prevention or treatment of disorders such as rickets and osteomalacia and are of value in the treatment of both vitamin D responsive and vitamin D resistant diseases such as hypoparathyroidism, hypophosphataemia, hypocalcaemia and/or associated bone disease, renal disorders or renal failure and hypocalcaemic tetany. Furthermore, the activity of these compounds and their rapid onset and termination of activity render them of value in cases where vitamin D should be avoided because of its cumulative toxicity, in particular in the treatment of disorders such as vitamin D resistant rickets, renal osteodystrophy, steatorrhea, biliary cirrhosis and other malfunctions of absorption, osteoporosis, secondary hypocalcaemia and/or bone disease arising from dysfunction of the liver, kidneys or gastrointestinal tract, and secondary hypocalcaemia, osteoporosis or other bone diseases resulting from treatment with steroids, such as corticoids, diphenylhydantoin, barbiturates such as phenylbarbitone, and related drugs, which prove refractory to conventional compounds such as vitamin D$_3$.

Processes for the preparation of 1α-hydroxyvitamin D$_3$, and the analogues thereof have been described in the literature, but the yield obtained is low and in certain cases a mixture of products is obtained from which it is very difficult to separate the desired product. Most published processes involve the preparation of a suitably substituted steroidal 5,7-diene followed by the known photochemical and thermal isomerization to the desired 1-hydroxy vitamin D analogue. These processes are multistage, complex and give small yields thus rendering them uneconomic for commercial production. The direct allylic hydroxylation of vitamin D$_3$ with selenium dioxide is described by Pelc B; (1977) Steriods 30, 193–201, but the yield of hydroxylated products does not exceed 5% and it is very difficult to separate the various products of the mixture. Similar results were obtained by Deluca H. F. et al. Proc. Natl. Acad. Sci. U.S.A. Vol 75 No. 5 pp. 2080–2081 (May 1978) and the preparation of 1α-hydroxy vitamin D from 3,5-cyclovitamin D described therein also involves a multistage low yield process.

Although, in view of the very high activity of 1α-hydroxy vitamin D$_3$, and the analogues thereof, processes having relatively low yields, e.g. of the order of 15%, may be sufficiently economic for commercial production, known processes are not capable of achieving even these low yields, and are not therefore well adapted for commercial production.

There is therefore a need for a process which will enable 1-hydroxyvitamin D compounds to be prepared more simply and/or in higher yields than hitherto possible, thus providing a process which would be sufficiently economic for commercial production.

The present invention is based on the discovery that 1-hydroxy 5,6-trans vitamin D compounds may be prepared in relatively high yield by oxidation of 5,6-trans vitamin D compounds using a selenite ester or selenium dioxide or selenous acid in the presence of an alcohol.

It is believed that the oxidant is always a selenite ester. Thus where it is desired to effect the oxidation reaction by the use of selenium dioxide or selenous acid and an alcohol it is believed that the selenite ester oxidant is formed by in situ reaction of the selenium dioxide or selenous acid with the alcohol.

Thus according to one feature of the present invention there is provided a process for the preparation of 1-hydroxy-5,6-trans vitamin D compounds which comprises oxidising a 1-unsubstituted 5,6-trans vitamin D compound using a selenite ester.

The invention also provides a corresponding process of oxidising a 5,6-trans vitamin D compound with selenium dioxide or selenous acid and an alcohol.

The 5,6-trans vitamin D compounds using as starting materials may, for example, be represented by the formula:

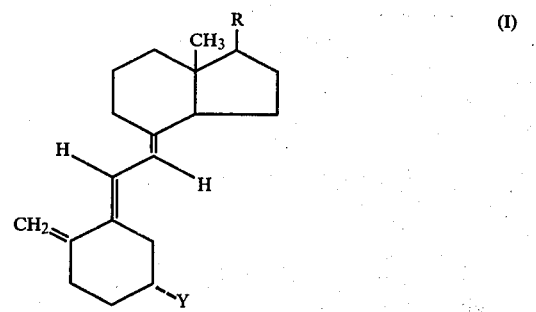

(I)

wherein Y represents a hydrogen atom or a hydroxyl or protected hydroxyl group and R represents a group of the formula:

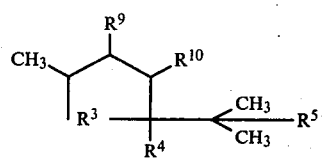

wherein R$^9$ and R$^{10}$, which may be the same or different, each represents a hydrogen or halogen atom or a hydroxy or protected hydroxy group or together form a carbon-carbon bond or an epoxy group, R$^3$ and R$^5$, which may be the same or different, each represents a hydrogen or halogen atom or a hydroxy or protected hydroxy group, and R$^4$ represents a hydrogen or halogen atom or a methyl or ethyl group, or R$^3$ and R$^4$ together represent a keto or protected keto group.

Where Y represents a protected hydroxyl group this may be an esterified or etherified hydroxyl group e.g. an alkanoyloxy group having 1 to 6 carbon atoms such as an acetoxy, propionyloxy, isobutyryloxy or pivaloxy group, an aroyloxy group having 7 to 15 carbon atoms e.g. a benzoyloxy or 4-phenylazobenzoyloxy group, a lower alkoxy group having 1 to 6 carbon atoms which may be interrupted by an oxygen atom such as a methoxy or methoxymethoxy group, a tetrahydropyranyloxy group or a trihydrocarbylsilyloxy group e.g. with 3 to 9 carbon atoms such as a trimethylsilyloxy group.

Although such protected forms are in general physiologically active, the free hydroxy forms are preferred for use in medicine. The protecting groups may be deprotected e.g. by conventional methods which methods are well documented in the literature. Thus, acyloxy groups of esters may be removed by basic hydrolysis, e.g. with alkali metal alkoxide in an alkanol. Ether groups, e.g. silyloxy groups, may be removed by acid hydrolysis or treatment with tetra-alkyl ammonium fluorides.

A 5,6-trans starting compound of formula I may, for example, be used in which the 17-side chain R represents the group

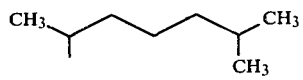

as in vitamin D$_3$.

The 5,6-trans vitamin D compound will, in general, be formed by isomerisation of the corresponding natural 5,6-cis compound, for example using conventional methods such as treatment with iodine, a Lewis acid such as BF$_3$ or diphenyldiselenide.

The oxidation of 5,6 trans vitamin D compounds according to the invention may take place in the presence of the corresponding 5,6-cis isomers, for example a mixture resulting from incomplete isomerisation of the 5,6-cis starting compound. Although direct oxidation of 5,6-cis isomers with selenium dioxide tends to yield large quantities of unwanted by-products, as is seen from the poor results reported in the prior art (where no alcohol was present), this reaction is far slower than the allylic oxidation of the trans-isomer; the cis-isomer is thus largely either left unoxidised or is isomerised.

In this connection we have found that if the starting vitamin D compounds do not have a bulky group present in the 3-position e.g. have a free 3-hydroxyl group or a 3-hydroxyl group protected by a lower (i.e. C$_{1-6}$) ester or ether such as an acetate or methyl ether, the initial 5,6-cis vitamin D compounds are isomerised in situ in the oxidation reaction and thus it may not be necessary to effect the isomerisation in a separate step prior to the oxidation.

We have also found, however, that where a bulky group, for example, a bulky ester group such as a pivalyloxy, isobutyryloxy, benzoyloxy or 4-phenylazobenzoyloxy group, is present in the 3-position; 5,6-cis vitamin D compounds do not isomerise satisfactorily under the conditions of the oxidation.

Although in these cases the 5,6-trans starting material has to be prepared by isomerisation in a separate step prior to oxidation, we have found that such 5,6-cis vitamin D compounds having bulky groups in the 3-position are oxidised very slowly indeed by selenium dioxide. It is thus possible to prepare a mixture, e.g. an equilibrium mixture, of the 5,6-cis and 5,6-trans isomers and to continue the oxidation with selenium dioxide until a substantial amount e.g. at least 60%, preferably about 80%, of the 5,6-trans isomer has been oxidised. In this connection the course of the reaction may be monitored by, for example, thin layer chromatography. The unreacted 5,6-cis vitamin D analogue may then, if desired, be subjected to another isomerisation step and used in the oxidation reaction again. In these circumstances it is unnecessary to separate mixtures of cis and trans isomers prior to the oxidation. It is especially advantageous that there is no need to separate cis and trans isomers prior to the oxidation reaction, since isomerization of the cis to the trans isomers inevitably results in an equilibrium mixture in which the ratio of trans to cis isomers is 3:2.

The alcohol used in conjunction with the selenium dioxide or selenous acid is preferably a lower alkanol, for example having 1 to 9 carbon atoms and being substituted by at least one, preferably one or two, hydroxy groups and which may carry one or more aryl groups having 6–9 carbon atoms. Where the lower alkanol is substituted by two hydroxy groups the hydroxy groups are preferably on adjacent carbon atoms (vicinal diols) or are on different carbon atoms which atoms are separated by a further carbon atom e.g. 1,2-ethanediol, 1,3-propanediol or 1,2-dihydroxy-3-methyl-butane. Preferred lower alkanols include ethanol and more especially methanol.

Where it is desired to effect the oxidation reaction using a selenite ester, the ester preferably has the formula:

$$R^1O—Se(O)—OR^2 \qquad (II)$$

wherein $R^1$ and $R^2$, which may be the same or different, each represents a hydrogen atom or an alkyl group with 1 to 9 carbon atoms or an aralkyl group having 1–9 carbon atoms in the alkyl portion and 6–9 carbon atoms in the aryl portion, with the proviso that at least one of $R^1$ and $R^2$ represents an alkyl or aralkyl group; or $R^1$ and $R^2$ together represent an alkylene group with 2 to 9 carbon atoms.

An ester of formula II may thus, for example, be used in which $R^1$ and $R^2$ together represent an ethylene or n-propylene chain. It is especially preferred, however, to use a compound of formula II in which one of $R^1$ and $R^2$ represents an alkyl group with 1 to 4 carbon atoms. Where $R^1$ and $R^2$ each represent alkyl or aralkyl groups $R^1$ and $R^2$ are normally the same, for example methyl, ethyl or benzyl groups. Diesters are preferred and $R^1$ and $R^2$ are preferably both alkyl groups or together represent an alkylene chain.

Although not essential, it is advantageous to effect the oxidation reaction using a selenite ester in the presence of an alcohol, preferably the alcohol from which the selenite ester is formed.

Regardless of whether the oxidation is effected using selenium dioxide or selenous acid in the presence of an alcohol or using a selenite ester, the oxidation reaction may, if desired, be effected in the additional presence of a co-solvent, for example an ether such as diethyl ether or a chlorinated hydrocarbon such as chlorobenzene. It may also be advantageous to effect the oxidation in the presence of acetonitrile which facilitates solution of the starting materials. Water may also be present in small quantities but is preferably absent.

The oxidation reaction is, in general, conveniently effected at a temperature from about ambient temperature (e.g. about 10°–25° C.) up to the boiling temperature of the reaction mixture.

The process of the present invention as described above has been found to result in yields of about 15–20% which yields are sufficiently high to render such processes economic for commercial production having regard to the high activity of 1α-hydroxyvitamin D compounds. In a further preferred embodiment of the present invention we have been able to increase still further the yield of 1-hydroxyvitamin D compounds by the use of a co-oxidant capable of oxidising Se$^{II}$ compounds to Se$^{IV}$ compounds. Indeed we have achieved yields as high as 60% by the use of such co-oxidants. Co-oxidants include for example, the metal salts of per acids, for example the metal salts of periodic acid, preferably the alkali metal salts of periodic acid, especially sodium metaperiodate. Certain alkyl hydroperoxides and tertiary amine oxides have been found to be especially advantageous for use as co-oxidants in view of the relatively clean oxidation reaction which can be effected under mild conditions, e.g. at ambient conditions, few contaminating by-products being formed.

The hydroperoxides of particular interest as co-oxidants are tertiary alkyl hydroperoxides in which the alkyl moiety may, if desired, by substituted by one or more aryl groups. Thus, for example, the hydroperoxide may have the formula

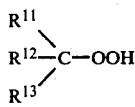

in which $R^{11}$, $R^{12}$ and $R^{13}$, which may be the same or different, each represent alkyl e.g. methyl or aralkyl e.g. benzyl groups, the hydroperoxide advantageously having from 4 to 16 carbon atoms e.g. t-butyl hydroperoxide.

The tertiary amine oxides of particular interest as co-oxidants are non-aromatic tertiary amine oxides, for example compounds of the formula:

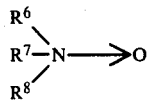

wherein $R^6$, $R^7$ and $R^8$, which may be the same or different, each represents an alkyl or aralkyl group or any two of $R^6$, $R^7$ and $R^8$ may represent, together with the nitrogen atom to which they are attached, a saturated heterocyclic group which may contain one or more further hetero atoms, for example one or more nitrogen, oxygen or sulfur atoms, the amine oxide advantageously having 3-15 carbon atoms. Thus for example the tertiary amine oxide may be a trialkylamine or a heterocyclic compound such as N-methyl morpholine N-oxide.

1 to 2.5, preferably about 2, molecular equivalents of the co-oxidant are conveniently used per molecular equivalent of the 5,6-trans starting material used.

The selenium dioxide is conveniently used in an amount ranging from 0.3 to 1.5, preferably about 1.0 molecular equivalents per molecular equivalent of 5,6-trans starting material. Where no co-oxidant is used the ratio of selenium dioxide to 5,6-trans starting material is preferably about 1:1. Selenous acid is conveniently used in the same proportions.

The oxidation reaction normally will yield predominantly 1α-hydroxy-5,6-trans vitamin D compounds but minor quantities of its β-isomer may be formed and where a small group is present at the 3-position, also minor quantities of 1α- and 1β-hydroxyvitamin $D_3$ cis-isomer. Yields of 1α-hydroxy-5,6-transvitamin $D_3$ of the order of 44% have been obtained using 5,6-transvitamin D derivatives having a relatively bulky ester grouping at the 3-position and using sodium metaperiodate as co-oxidant a further 18% of 1β-hydroxy-5,6-transvitamin D being formed simultaneously.

Selenite esters have, for example, been described in "Comprehensive Organic Chemistry," Pergamon 1st Ed, Vol 3; Editor: D. Neville Jones; pp 525 et seq.

Thus, for example, the above-described selenite esters may be prepared by reacting selenium dioxide or selenous acid with the appropriate alcohol, e.g. (1) of the formula $R^1OH$ or $R^2OH$ (wherein $R^1$ and $R^2$ are as hereinbefore defined) in which case a compound of formula II is normally prepared in which $R^1$ and $R^2$ are the same or (2) a diol in which the alkyl moiety is as hereinbefore defined for $R^1$ and $R^2$ together.

1-Hydroxytransvitamin D compounds may, if desired, be converted into the corresponding cis compound by isomerization methods well known from the literature e.g. by treatment with iodine, a Lewis acid or diphenyldiselenide.

The 1α-hydroxy compounds are of particular interest in that 1α-hydroxyvitamin $D_3$ (cis-isomer) and many of its analogues are of great value in medicine while the 1α-hydroxy-5,6-transvitamin D compounds may either be converted into their 5,6-cis isomers as described herein or used as an intermediate in the production of 1α-hydroxy-dihydrotachysterols by conventional methods well known in the literature. The 1β-hydroxymaterial may be separated from the 1α-hydroxymaterial by conventional methods such as chromatography or even by direct crystallisation. The undesired 1β-isomer may if desired subsequently be converted into the 1α-isomer according to known isomerisation techniques e.g. directly or, more preferably, by oxidation with an allylic oxidant, e.g. manganese dioxide, to the corresponding 1-oxo steroid followed by stereospecific reduction with a metal hydride e.g. lithium aluminium hydride or sodium borohydride.

The isomerisation of 1β-hydroxy-5,6-trans vitamin D compounds to the desired 1α-hydroxy-5,6-cis vitamin D compounds thus requires two isomerization steps; the isomerisation at the 1-position is preferably effected first.

The present invention thus also relates to the isomerisation of a 1-hydroxy-5,6-trans vitamin D compound obtained according to the above-described process to the 1α-hydroxy-5,6-vitamin D compound (i.e. the 5,6-cis isomers).

The products of the process of the present invention, e.g. 1α-hydroxyvitamin D compounds (i.e. 5,6-cis isomers) especially 1α-hydroxyvitamin $D_3$, may be formulated into pharmaceutical compositions in the conventional manner.

Thus according to a further feature of the present invention there are provided pharmaceutical compositions comprising a 1α-hydroxy vitamin D compound, especially 1α-hydroxyvitamin $D_3$, prepared according to the process hereinbefore described as active ingredient in association with a pharmaceutical carrier or excipient.

In the following Examples which illustrate the present invention variation of concentration was found to have a noticeable effect on reaction rate. Yields were generally found to be in the range 30 to 35% based on the recovered starting material. The high pressure liquid chromatography (HPLC) conditions are as follows:

| Support - Porasil A | | |
|---|---|---|
| Solvents - dihydroxyvitamins: | EtOAc | 75% |
| | Benzene | 25% |

| - hydroxyacetoxyvitamins: | Et$_3$N | 0.1% |
| | Benzene | 88% |
| | EtOAc | 12% |
| | Et$_3$N | 0.1% |

EXAMPLE 1

Reaction of Transvitamin D$_3$ with selenium dioxide

Transvitamin D$_3$ (1 g) was dissolved in dry methanol (30 ml) under an atmosphere of argon. Selenium dioxide [solid (280 mg)] and solid sodium metaperiodate (800 mg) were added to the stirred solution and the mixture was brought raidly to reflux whilst stirring vigorously. The appearance of product was followed by thin layer chromatography (t.l.c.). When the reaction was completed (usually 10–20 min.) the reaction mixture was cooled in a water bath, then diluted with ether, washed twice with 5% sodium bicarbonate solution dried (MgSO$_4$), filtered and evaporated in vacuo. The residue was taken up in hexane/benzene and chromatographed over silica gel (10 g) (medium pressure-rapid chromatography) to afford a mixture of 1-hydroxylated vitamins (330 mg). The mixture of vitamins was taken up in hexanes, and filtered yielding 1α,3β-dihydroxytransvitamin D$_3$ (120 mg). The mother liquors were chromatographed using high pressure liquid chromatography to yield in order of elution:

1α,3β-dihydroxytransvitamin D$_3$
1α,3β-dihydroxycisvitamin D$_3$
1β,2β-dihydroxycisvitamin D$_3$
1β,3β-dihydroxytransvitamin D$_3$ the latter was obtained as the second most abundant isomer.

Oxidation of vitamin D$_3$ under identical conditions afforded a similar result.

EXAMPLE 2

Reaction of vitamin D$_3$ with selenium dioxide

Vitamin D$_3$ (2.4 g) was dissolved in dry methanol (70 mg) under a flow of argon. To the stirred solution was added selenium dioxide (672 mg) and sodium metaperiodate (1.92 g). The solution was rapidly brought to reflux whilst stirring vigorously. The reaction monitored by t.l.c. When the reaction was complete it was worked up as described above and chromatographed on silica gel (10 g) to afford a mixture of 1-hydroxy vitamins. Filtration from hexanes, gave as a white crystalline solid 1α,3β-dihydroxytrans-vitamin D$_3$ (251 mg). High pressure liquid chromatography (HPLC) separation of the residue gave 1α,3β-dihydroxytrans-vitamin D$_3$ (49 mg), 1α,3β-dihydroxycisvitamin D$_3$ (38 mg), 1β,3β-dihydroxycisvitamin D$_3$ (32 mg) and as the most polar vitamin 1β,3β-dihydroxytransvitamin D$_3$ (83 mg).

EXAMPLE 3

Reaction of transvitamin D$_3$ acetate with selenium dioxide

Transvitamin D$_3$ acetate (0.75 g) was dissolved in dry methanol (21 ml) under an atmosphere of argon (required warming to achieve solubility). Selenium dioxide (155 mg) and sodium metaperiodate (409 mg) were added to the solution. The solution was rapidly brought to reflux whilst stirring vigorously, and followed by t.l.c. When the reaction was judged complete (approx. 17 mins) it was worked up as described above and chromatographed to yield recovered starting material (72 mg) cis to trans ratio 2:3:4) and 1-hydroxylated vitamins (345 mg) (49%). The mixture was chromatographed on HPLC to yield 1β-hydroxy-3β-acetoxycisvitamin D$_3$ (34 mg); 1α-hydroxy-3β-acetoxycisvitamin D$_3$ (64.2 mg); and as a mixture 1α and 1β-hydroxy-3β-acetoxytransvitamin D$_3$ (206 mg). Separation of 1α- and 1β-hydroxy-3β-acetoxytransvitamin D$_3$ has been achieved on medium pressure rapid column chromatography.

EXAMPLE 4

Reaction of transvitamin D$_3$ 3β-pivalate with selenium dioxide

Under conditions similar to those outlined above 3β-pivaloyltransvitamin D$_3$ (445 mg) was reacted with selenium dioxide (105 mg) and sodium metaperiodate (420 mg) in dry methanol (15 ml) to afford after column chromatography recovered starting material (131 mg), followed by 1β-hydroxy-3β-pivaloyltransvitamin D$_3$ (61.2 mg, 18%) and 1α-hydroxy-3β-pivaloyltransvitamin D$_3$ (143 mg, 44%), as the only hydroxylated products.

EXAMPLE 5

Reaction of 4-Phenylazobenzoyltransvitamin D$_3$ with selenium dioxide

4-Phenylazobenzoyltransvitamin D$_3$ (500 mg) is reacted with selenium dioxide and sodium metaperiodate in dry methanol/chloroform to yield recovered starting material (64 mg) 1β-hydroxy-3β-(4-phenylazobenzoyl)-transvitamin D$_3$ (70 mg) and 1α-hydroxy-3β-(4-phenylazobenzoyl)-transvitamin D$_3$ (157 mg).

EXAMPLE 6

Oxidation of transvitamin D$_3$ benzoate with the cyclic selenite of 1,2-dihydroxy-3-methyl-butane Transvitamin D$_3$ benzoate (495 mg) in dry ether (12 ml, was treated at room temperature with t-butyl hydroperoxide in ether (170 µl) and the title selenite (60 µl) under an atmosphere of argon. After 1 hour further t-butyl hydroperoxide and selenite were added as above. After 4 hours the work up described in Example 1 afforded 132 mg. of unreacted starting material and 170 mg. of the hydroxylated product.

EXAMPLE 7

Oxidation of transvitamin D$_3$ benzoate with the cyclic selenite of ethylene glycol Trans vitamin D$_3$ benzoate (220 mg) in ether (5 ml) was treated at room temperature with t-butyl hydroperoxide (124 µl) and the title selenite (33 µl) under an atmosphere of argon. After 2 hours the work up described in Example 1 afforded 70 mg of unreacted starting material and 57 mg of hydroxylated product.

EXAMPLE 8

Oxidation of transvitamin D$_3$ benzoate (a) Oxidation using sodium metaperiodate and diethyl selenite in methanol Transvitamin D$_3$ (320 mg) in a 3:1 mixture of methanolhexane (12 ml) was heated to reflux. Diethyl selenite (40 µl) and sodium metaperiodate (280 mg) were added. After refluxing for 20 mins., the reaction mixture was cooled rapidly, poured into ether and partitioned between ether and dilute aqueous sodium bicarbonate solution. The aqueous layer was extracted twice with ether. The combined ethereal layers were washed with water until neutral, dried and ether was evaporated to give an oil which was chromatographed to yield 75 mg of starting material, 15 mg of 1β-hydroxy-transvitamin D₃ 3β-benzoate (A) as an oil and 80 mg of 1α-hydroxy-transvitamin D₃ 3β-benzoate, (B), as an oil.

NMR of (A): 0.46(3H.s), 0.80, 0.90 (methyls), 4.29(1H,m), 5.10(1H,br.s.) 5.20(1H, br.s.), 5.23(1H,m), 5.86(1H,d,J 11. 5 Hz), 6.68(1H,d, J 115 Hz), 7.53(3H,m), 8.06(2H,m).

NMR of (B): 0.40(3H,s), 0.80, 0.90 (methyls), 4.57(1H,m), 5.03(1H,br.s) 5.13(1H, br.s.), 5.50(1H,m), 5.80 (1H, d,. J 11.5 Hz), 6.60 (1H,d, J 11.5 Hz), 7.43 (3H, m), 8.00 (2H,m).

(b) Oxidation with diethyl selenite in methanol and tert-butylhydroperoxide

A solution of transvitamin D₃ (370 mg, in a 1:3 mixture of methanol-ether (8 ml) was oxidized at room temperature using diethyl selenite (95 μl) and 70% aqueous tert-butylhydroperoxide (dried over 3 A molecular sieves 230 μl) at room temperature. The work up described in (a) and chromatography yielded 124 mg of starting material and 137 mg of (A) and (B).

(c) Oxidation with diethyl selenite and N-methyl morpholine N-oxide

A solution of transvitamin D₃ benzoate (950 mg), diethyl selenite (250 μl), and N-methyl morpholine N-oxide (500 mg) in a 1:3 mixture of methanol-ether (16 ml) was allowed to stand overnight at 22° C. The reaction mixture was worked up as usual. After column chromatography, 190 mg of starting material, 50 mg of pure (A) and 55 mg of an approximately 1:1 mixture of (A) and (B), and 260 mg of pure (B) were obtained.

We claim:

1. A process for the preparation of 1-hydroxy-5,6-trans vitamin D compounds which comprises oxidising a 1-unsubstituted 5,6-trans vitamin D compound using a selenite ester having the formula:

R¹O—Se(O)—OR² (II)

wherein R¹ and R², which may be the same or different, each represents a hydrogen atom or an alkyl group with 1 to 9 carbon atoms or an aralkyl group having 1–9 carbon atoms in the alkyl portion and 6–9 carbon atoms in the aryl portion, with the proviso that at least one of R¹ and R² represents an alkyl or aralkyl group; or R¹ and R² together represent an alkelene group with 2 to 9 carbon atoms.

2. A process for the preparation of 1-hydroxy-5,6-trans vitamin D compounds which comprises oxidising a 1-unsubstituted 5,6-trans vitamin D compound using selenium dioxide in the presence of a lower alkanol, lower alkanol substituted by at least 1-hydroxy, aryl group having 6 to 9 carbon atoms or combinations thereof.

3. A process as claimed in claim 2 wherein the 5,6-trans vitamin D compound used as starting material has the formula:

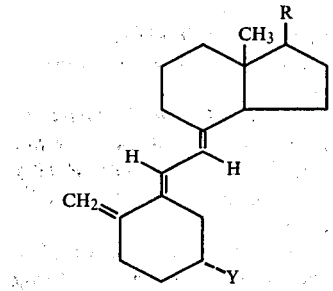

wherein Y represents a hydrogen atom or a hydroxyl or protected hydroxyl group and R represents a group of the formula:

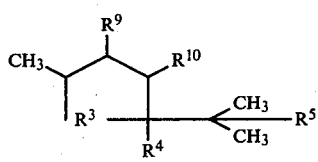

wherein R⁹ and R¹⁰, which may be the same or different, each represents a hydrogen or halogen atom or a hydroxy or protected hydroxy group or together form a carbon-carbon bond or an epoxy group, R³ and R⁵, which may be the same or different, each represents a hydrogen or halogen atom or a hydroxy or protected hydroxy group, and R⁴ represents a hydrogen or halogen atom or a methyl or ethyl group, or R³ and R⁴ together represent a keto or protected keto group.

4. A process as claimed in claim 3 wherein a compound of formula I is used in which R represents the group:

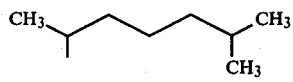

5. A process as claimed in claim 2 wherein 5,6-trans vitamin D compound used as starting material is prepared by in situ isomerization of the corresponding 5,6-cis vitamin D compound under the conditions of the oxidation.

6. A process as claimed in claim 2 in which oxidation is effected in the presence of co-oxidant capable of oxidising Se^{II} compounds to Se^{IV} compounds.

7. A process as claimed in claim 2 wherein the 1-hydroxy-5,6-trans vitamin D compound thus formed is isomerized whereby a 1α-hydroxy-5,6-cis vitamin D compound is obtained.

8. A process as claimed in claim 2 wherein the oxidation is effected using selenium dioxide in the presence of an alkanol having 1 to 9 carbon atoms.

9. A modification of a process as claimed in claim 2 wherein the oxidation is effected using a selenite ester of the formula:

R¹O—Se(O)—OR² II wherein R¹ and R², which may be the same or different, each represents a hydrogen atom or an alkyl group with 1 to 9 carbon atoms with the proviso that at least one of R¹ and R² represents an alkyl group; or R¹ and R² together represent an alkylene group with 2 to 9 carbon atoms.

10. A process as claimed in claim 9 wherein $R^1$ and $R^2$, which are the same, each represent an alkyl group with 1 to 4 carbon atoms.

11. A process as claimed in claim 1 wherein the oxidation is effected in the presence of a metal salt of a per acid, an alkyl hydroperoxide in which the alkyl moiety contains from 4 to 16 carbon atoms, or a non-aromatic tertiary amine oxide as co-oxidant.

12. A process for the preparation of 1-hydroxy-5,6-trans vitamin D compounds which comprises oxidising a 1-unsubstituted 5,6-trans vitamin D compound using selenous acid in the presence of a lower alkanol, lower alkanol substituted by at least 1-hydroxene, aryl group having 6–9 carbon atoms or combinations thereof.

13. A process as claimed in claim 11 wherein the cooxidant is sodium metaperiodate.

14. A process as claimed in claim 8 wherein the alkanol is methanol.

15. A process as claimed in claim 2 wherein the alkanol is dry methanol and sodium metaperiodate is present as a co-oxidant.

* * * * *